United States Patent [19]

Sicheneder et al.

[11] Patent Number: 5,719,294
[45] Date of Patent: Feb. 17, 1998

[54] PROCESS FOR PREPARING N-CYCLOHEXYLTHIOPHTHALIMIDE

[75] Inventors: Adolf Sicheneder, Hohenlockstedt; Wilfried Nolte, Odenthal; Harro Schlesmann, Odenthal; Thomas Kleiner, Odenthal, all of Germany

[73] Assignee: Bayer AG, Leverkusen, Germany

[21] Appl. No.: 747,851

[22] Filed: Nov. 13, 1996

[30] Foreign Application Priority Data

Nov. 24, 1995 [DE] Germany .................. 195 43 863.9

[51] Int. Cl.$^6$ .................................................. C07D 209/48
[52] U.S. Cl. .................................................. 548/475
[58] Field of Search .................................................. 548/475

[56] References Cited

FOREIGN PATENT DOCUMENTS 198080  6/1982  Czechoslovakia .

*Primary Examiner*—Richard L. Raymond
*Attorney, Agent, or Firm*—Connolly & Hutz

[57] ABSTRACT

The preparation of N-cyclohexylthiophthalimide from cyclohexylsulphenyl chloride and phthalimide can be reproduced more reliably if the cyclohexylsulphenyl chloride is prepared in sire by chlorinating dicyclohexyl disulphide.

15 Claims, No Drawings

PROCESS FOR PREPARING N-CYCLOHEXYLTHIOPHTHALIMIDE

The invention relates to a process for preparing N-cyclohexylthiophthalimide by reacting cyclohexyl disulphide, phthalimide and chlorine in the presence of a base.

The compound prepared according to the invention is used to retard premature vulcanisation of natural and/or synthetic rubbers.

N-cyclohexylthiophthalimide can be prepared by reacting phthalimide with cyclohexylsulphenyl chloride. Cyclohexylsulphenyl chloride can be produced by chlorination of cyclohexyl mercaptan or dicyclohexyl disulphide. In, the preferred procedure for preparing cyclohexylsulphenyl chloride, cyclohexyl mercaptan is suspended in water and oxidised with hydrogen peroxide, the dicyclohexyl disulphide produced is extracted with an organic solvent, preferably an optionally chlorinated hydrocarbon which is liquid at room temperature such as toluene or hexane, and the dissolved disulphide is chlorinated with chlorine to give cyclohexylsulphenyl chloride. The reactions thus correspond to the following scheme:

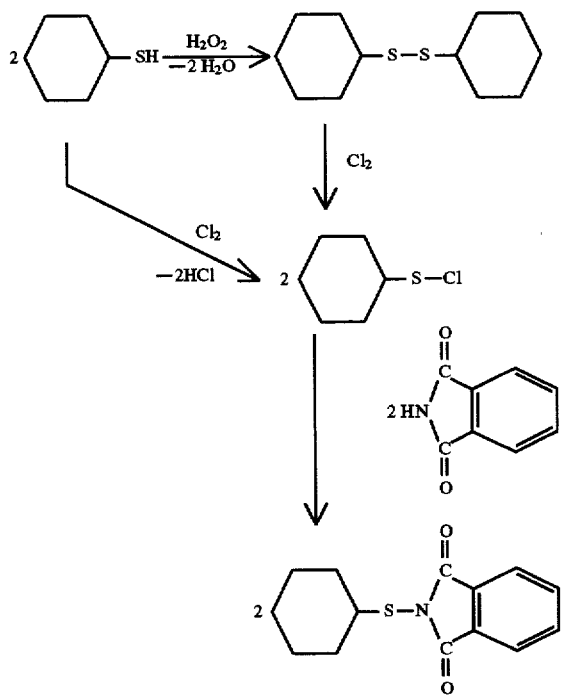

In the last stage of the process, according to U.S. Pat. No. 3,579,460, phthalimide dissolved in dimethyl formamide is reacted with cyclohexylsulphenyl chloride dissolved in pentane, in the presence of an equimolar amount of a tertiary amine. Precipitation of the final product with a large mount of water leads to high expenditure on recovering the amine and the solvent, working up the mother liquor and a drying procedure.

EP-A 47 912 describes a process for preparing N-cyclohexylthio-phthalimide by reacting phthalimide in aqueous suspension with cyclohexylsulphenyl chloride dissolved in an organic solvent, in the presence of an alkali metal or alkaline earth metal hydroxide. The reproducibility of the yields, however, may not always be satisfactory.

Surprisingly, it has now been found that the yields are reproducible within very narrow limits if cyclohexylsulphenyl chloride, prepared in situ from dicyclohexyl disulphide in accordance with the reaction scheme

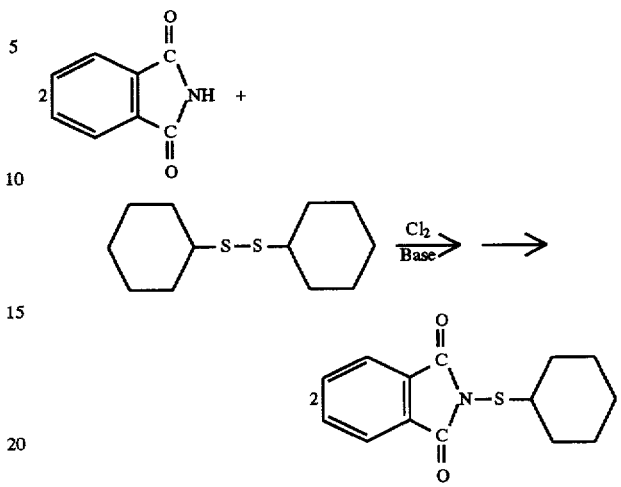

is allowed to react with phthalimide suspended in an organic solvent, in the presence of a base. In this case, there is no need to handle the hydrolysis-sensitive cyclohexylsulphenyl chloride solution. This produces clear improvements with regard to the protection of the environment and occupational safety.

The invention thus provides a process for preparing N-cyclohexylthiophthalimide by reacting cyclohexylsulphenyl chloride with phthalimide in the presence of a base, characterised in that cyclohexylsulphenyl chloride is prepared, in the presence of phthalimide, from dicyclohexyl disulphide and chlorine.

The molar ratio dicyclohexyl disulphide/phthalimide may be 1:1.9 to 1:2.2, preferably 1:2 to 1:2.1.

The molar ratio chlorine/dicyclohexyl disulphide may be 1:1 to 1.2:1, preferably 1:1 to 1.05:1.

Alkali metal and alkaline earth metal hydroxides (preferably used as aqueous solutions) and tertiary amines are preferred as bases. The molar ratio base/phthalimide may vary between wide limits; it is generally 1:1 to 1.3:1, preferably 1.05:1 to 1.1:1.

Preferred alkali metal and alkaline earth metal hydroxides include sodium, potassium, lithium and calcium hydroxide. Caustic soda solution in a concentration of 5 to 40 wt. % is preferably used. It is especially advantageous if the density of the hydroxide solution used is in the range 1.0 to 1.2 g/ml at the desired reaction temperature.

Preferred tertiary amines correspond to the formula $$NR^1R^2R^3$$

in which $R^1$–$R^3$, independently of each other, represent $C_2$–$C_6$alkyl, $C_6$–$C_{12}$-cycloalkyl, $C_7$–$C_{12}$-arylalkyl or $C_6$–$C_{12}$-aryl groups, wherein two of these groups together may also form a $C_4$–$C_7$-alkylene group, optionally interrupted by an oxygen atom.

Preferred tertiary mines include, for example, triethylamine, dimethylbenzylamine and N-ethylmorpholine.

The process according to the invention can be performed in such a way that, for example, chlorine is passed into a mixture of dicyclohexyl disulphide and phthalimide in an aprotic organic solvent and the cyclohexylsulphenyl chloride prepared in situ in that way. Reaction of the sulphenyl chloride with phthalimide takes place in the presence of a base. The base is generally added after completing the chlorination reaction. However, chlorination may also be performed in the absence of phthalimide, which may be added later.

A wide range of solvents may be used. They include:

aromatic hydrocarbons, such as benzene and/or toluene, aliphatic hydrocarbons, such as hexane, heptane, octane and/or cyclohexane, chlorinated hydrocarbons, such as $CCl_4$, dichloroethylene and/or chlorobenzene, polar, aprotic solvents, such as DMF and/or DMSO.

Toluene, hexane and/or cyclohexane are preferably used.

The amounts of solvent used are generally in the range 600 to 1,500 wt. % with reference to phthalimide.

The process according to the invention may be performed at temperatures of −20° to 100°, preferably 0° to 20° C.

EXAMPLES

The parts mentioned in the following examples are parts by weight; percentage data refer to weight.

Example 1

The following are initially placed in a stirred vessel:

300 parts of toluene 40 parts of phthalimide 31 parts of dicyclohexyl disulphide.

The mixture is cooled to 5° C. Then, with stirring, 9.8 parts of chlorine are first introduced. Then 38.2 parts of dimethylbenzylamine are pumped in and stirring is continued for 15 minutes. The resulting solution is washed with 80 parts of hydrochloric acid (5% strength)

and the organic phase is then separated.

200 parts of toluene are distilled off under vacuum and the product is precipitated by adding hexane. The solid product is filtered off, washed with 30 parts of hexane and the product is then dried under vacuum.

Yield: 68 parts of N-(cyclohexylthio)-phthalimide=97% of theoretical, with respect to the dicyclohexyl disulphide used.

The concentration of pure substance is 98%.

Example 2

The following are initially placed in a stirred vessel;

300 parts of toluene 41 parts of phthalimide 30 parts of dicyclohexyl disulphide The mixture is cooled to 5° C. Then 9.5 parts of chlorine are introduced and then 115 parts of caustic soda solution (10% strength)

are pumped in and stirring continued for 30 minutes. After phase separation, the product is isolated from the organic phase in the same way as in example 1.

Yield: 66 parts of N-(cyclohexylthio)-phthalimide=97% of theoretical with reference to the dicyclohexyl disulphide used.

The concentration of pure substance is 99%.

We claim:

1. A process for preparing N-cyclohexylthiophthalimide by reacting cyclohexylsulphenyl chloride with phthalimide in the presence of a base, characterised in that the cyclohexylsulphenyl chloride is prepared from dicyclohexyl disulphide and chlorine in the presence of the phthalimide.

2. A process according to claim 1, wherein it is performed at a temperature of −20° to 100° C.

3. A process for preparing N-cyclohexylthiophthalimide according to claim 1, wherein the dicyclohexyl disulphide and phthalimide are used in a molar ratio of dicyclohexyl disulphide:phthalimide of from 1:1.9 to 1:2.2.

4. A process for preparing N-cyclohexylthiophthalimide according to claim 1, wherein the dicyclohexyl disulphide and phthalimide are used in a molar ratio of dicyclohexyl disulphide:phthalimide of from 1:2 to 1:2.1.

5. A process for preparing N-cyclohexylthiophthalimide according to claim 1, wherein the dicyclohexyl disulphide and chlorine are used in a molar ratio of chlorine:dicyclohexyl disulphide of from 1:1 to 1.2:1.

6. A process for preparing N-cyclohexylthiophthalimide according to claim 1, wherein the dicyclohexyl disulphide and chlorine are used in a molar ratio of chlorine:dicyclohexyl disulphide of from 1:1 to 1.05:1.

7. A process according to claim 1, wherein said base is an alkali metal hydroxide.

8. A process according to claim 1, wherein said base is an alkaline earth metal hydroxide.

9. A process according to claim 1, wherein said base is a tertiary amine.

10. A process according to claim 1, wherein the base and phthalimide are used in a molar ratio of base:phthalimide of from 1:1 to 1.3:1.

11. A process according to claim 1, wherein the base and phthalimide are used in a molar ratio of base:phthalimide of from 1.05:1 to 1.1:1.

12. A process according to claim 1, wherein said base is an aqueous solution of an alkali metal hydroxide or an alkaline earth metal hydroxide.

13. A process according to claim 1, wherein said base is a tertiary amine corresponding to the formula $NR^1R^2R^3$ in which $R^1$–$R^3$, independently of each other, represent $C_2$–$C_6$-alkyl, $C_6$–$C_{12}$-cycloalkyl, $C_7$–$C_{12}$-arylalkyl or $C_6$–$C_{12}$-aryl groups.

14. A process according to claim 1, wherein said base is a tertiary amine selected from the group consisting of triethylamine, dimethylbenzyl amine and N-ethylmorpholine.

15. A process according to claim 1, wherein said base is a tertiary amine corresponding to the formula $NR^1R^2R^3$ in which one of $R^1$, $R^2$ or $R^3$ represents $C_2$–$C_6$-alkyl, $C_6$–$C_{12}$-cycloalkyl, $C_7$–$C_{12}$-arylalkyl or $C_6$–$C_{12}$-aryl and the remaining two R groups together form a $C_4$–$C_7$-alkylene group or a $C_4$–$C_7$-alkylene group interrupted by an oxygen atom.

* * * * *

UNITED STATES PATENT AND TRADEMARK OFFICE
CERTIFICATE OF CORRECTION

Page 1 of 2

PATENT NO. : 5,719,294
DATED : February 17, 1998
INVENTOR(S) : Adolf Sicheneder, et al.

It is certified that error appears in the above-identified patent and that said Letters Patent is hereby corrected as shown below:

On the cover page, section [56], References Cited, should be changed from:

"FOREIGN PATENT DOCUMENTS
198080    6/1982    Czechoslovakia"

to

--U.S. PATENT DOCUMENTS 3,579,460         05/1971         Kerwood       252/182

FOREIGN PATENT DOCUMENTS 198080         06/1982         Czechoslovakia
EP 0 047 912   03/1982         Europe

OTHER PUBLICATIONS

Orbit Abstract of EP 0 047 912 (03/24/82).

Chemical Abstracts, Vol. 118, No. 22, May 31, 1993, Columbus, OH, US; Abstract No. 214691e, Page 84; XP002024423 & CN-1063695.

Chemical Abstracts, Vol. 111, No. 7, August 14, 1989, Columbus, OH, US; Abstract No. 57537v, Page 741; XP002024425 & CS-254208.

UNITED STATES PATENT AND TRADEMARK OFFICE
CERTIFICATE OF CORRECTION

PATENT NO. : 5,719,294
DATED : February 17, 1998
INVENTOR(S) : Adolf Sicheneder, et al.

It is certified that error appears in the above-identified patent and that said Letters Patent is hereby corrected as shown below:

Chemical Abstracts, Vol. 98, No. 13, March 28, 1983, Columbus, OH, US; Abstract No. 107158h, Page 589; XP002024424 & CS-198080.

Chemical Abstracts, Vol. 117, No. 19, November 9, 1992, Columbus, OH, US; Abstract No. 191681q, Page 784; XP002024426 & CN-1059906.

Chemical Abstracts, Vol. 109, No. 11, September 12, 1988, Columbus, OH, US; Abstract No. 92777d, Page 687; XP002024427 & JP-A-62289561 (Mitsubishi Monsanto Chemical Co.), December 16, 1987.

Chemical Abstracts, Vol. 70, No. 13, March 31, 1969, Columbus, OH, US; Abstract No. 57337q, Page 315; XP002024428 and J. Org. Chem., 1969, 34(1), 51-5.--

In section [57], ABSTRACT, last line, the word "sire" should be --situ--.

Signed and Sealed this

Thirty-first Day of October, 2000

*Attest:*

Q. TODD DICKINSON

*Attesting Officer*     *Director of Patents and Trademarks*